United States Patent
Kim et al.

(10) Patent No.: US 9,880,126 B2
(45) Date of Patent: Jan. 30, 2018

(54) BIOSENSOR BASED ON CARBON NANOTUBE-ELECTRIC FIELD EFFECT TRANSISTOR AND METHOD FOR PRODUCING THE SAME

(75) Inventors: Jae-Ho Kim, Seongnam-si (KR); Sung-Wook Choi, Seongnam-si (KR); Jae-Hyeok Lee, Cheongwon-gun (KR); Gwang Hyeon Nam, Changwon-si (KR)

(73) Assignee: Ajou University Industry-Academic Cooperation Foundation, Suwon-si (KR)

(*) Notice: Subject to any disclaimer, the term of this patent is extended or adjusted under 35 U.S.C. 154(b) by 582 days.

(21) Appl. No.: 12/890,152

(22) Filed: Sep. 24, 2010

(65) Prior Publication Data
US 2012/0073992 A1    Mar. 29, 2012

(51) Int. Cl.
| | |
|---|---|
| *H01L 51/30* | (2006.01) |
| *G01N 27/414* | (2006.01) |
| *B82Y 10/00* | (2011.01) |
| *B82Y 15/00* | (2011.01) |
| *B82Y 30/00* | (2011.01) |
| *H01L 51/00* | (2006.01) |
| *H01L 51/05* | (2006.01) |

(52) U.S. Cl.
CPC .......... *G01N 27/4146* (2013.01); *B82Y 10/00* (2013.01); *B82Y 15/00* (2013.01); *B82Y 30/00* (2013.01); *H01L 51/0048* (2013.01); *B01J 2219/00653* (2013.01); *B01J 2219/00725* (2013.01); *H01L 51/0512* (2013.01)

(58) Field of Classification Search
CPC .... G01N 27/4146; B82Y 10/00; B82Y 15/00; B82Y 30/00; H01L 51/0048; H01L 51/0512; B01J 2219/00653; B01J 2219/00725

USPC ......... 205/777.5, 779, 787, 792; 257/59, 72, 257/420, 24, 462, E51.04, E51.052; 977/762; 438/49
See application file for complete search history.

(56) References Cited

U.S. PATENT DOCUMENTS

| | | | |
|---|---|---|---|
| 6,528,020 B1 * | 3/2003 | Dai et al. .................. | 422/98 |
| 2003/0134267 A1 | 7/2003 | Kang et al. ................ | 435/4 |

(Continued)

FOREIGN PATENT DOCUMENTS

| | | |
|---|---|---|
| JP | 2006-220513 | 5/2006 |
| JP | 2006-220513 | 8/2006 |

(Continued)

OTHER PUBLICATIONS

Star et al., "Electronic detection of specific protein binding using nanotube FET devices," *Nano Letters*, 3(4):459-463, 2003.

(Continued)

*Primary Examiner* — Magali P Slawski
*Assistant Examiner* — Kourtney R S Carlson
(74) *Attorney, Agent, or Firm* — Parker Highlander PLLC

(57) ABSTRACT

Disclosed are a biosensor, a method of producing the same, and a method of detecting a biomaterial through the biosensor. The biosensor includes a substrate, an insulating layer, source and drain electrodes formed on the insulating layer, a middle-discontinuous channel provided between the source and drain electrodes, and a detection area on which a detection target material is to be fixed, covering the middle-discontinuous channel.

12 Claims, 5 Drawing Sheets

(56) References Cited

U.S. PATENT DOCUMENTS

| | | | |
|---|---|---|---|
| 2007/0063304 A1* | 3/2007 | Matsumoto et al. | 257/462 |
| 2008/0063566 A1* | 3/2008 | Matsumoto et al. | 422/68.1 |
| 2008/0221806 A1* | 9/2008 | Bryant et al. | 702/22 |
| 2008/0259264 A1* | 10/2008 | Jin | 349/146 |
| 2011/0081724 A1* | 4/2011 | Swager et al. | 436/57 |

FOREIGN PATENT DOCUMENTS

| | | |
|---|---|---|
| KR | 10-0455284 | 10/2004 |
| KR | 10-2007-0058880 | 6/2007 |
| WO | WO 2006-024023 | 3/2006 |

OTHER PUBLICATIONS

Office Conmunication issued in Japanese Patent Application No. 2010-214375, dated Feb. 14, 2012. (English translation).

\* cited by examiner

BIOSENSOR BASED ON CARBON NANOTUBE-ELECTRIC FIELD EFFECT TRANSISTOR AND METHOD FOR PRODUCING THE SAME

ACKNOWLEDGEMENT

This research was supported by a grant (A090902) from Gyeonggi Technology Development Program funded by Gyeonggi Province.

BACKGROUND OF THE INVENTION

1. Field of the Invention

The present invention relates to a biosensor which comprises a substrate, an insulating layer, source and drain electrodes formed on the insulating layer, a middle-discontinuous channel provided between the source and drain electrodes, and a detection area covering the middle-discontinuous channel on which a target material to be detected is fixed, a method of producing the same, and a method of detecting a biomaterial using the biosensor. More particularly, the present invention relates to a biosensor detecting a target biomaterial, wherein a receptor is fixed on a detection area, the receptor is selectively coupled with a target biomaterial, while a contact resistance is changed by the selective coupling of the receptor with the target biomaterial, and thus the amount of an electric current flowing from a source electrode to a drain electrode is changed, when using a carbon nanotube-electric field effect transistor to detect a biomaterial, a method of producing the same, and a method of detecting a target biomaterial using the biosensor.

2. Description of Related Art

A biosensor may refer to "a system that converts information acquired from a target to be measured into a recognizable signal such as color, fluorescent, and electrical signals by using a biological element or copying a biological system." A biosensor may be constructed in various forms in accordance with a target material to be measured, a biological element fixed on the sensor, and the kind of a signal converter. For signal conversion, there have been used various physical and chemical techniques such as electrochemical, thermal, optical and mechanical techniques.

There have been various biosensors according to a target material to be measured, a biological element fixed on the sensor, and the kind of a signal converter. The first biosensor is known as a Glucose sensor made by using a dialysis membrane by Clark for measuring glucose in 1962. In the early stage, most of biosensors are made by fixing an enzyme on a signal converting device. However, sensors made using a monoclonal antibody, an antibody-enzyme conjugate, etc. have recently been developed with rapid development of molecular biology. Also, researches and development of chip sensors such as a DNA chip, a protein chip or the like for processing massive genetic information at super-high speed have become active, and a lot of efforts have been concentrated on the development of high-technology sensors in which molecular biotechnology, nanotechnology and information and communication technology are fused.

A biochip refers to a chip formed by fixing bio-molecules such as DNA, protein, etc. on a small substrate made of glass, silicon, nylon or a like. A DNA-fixed biochip is called as a DNA chip, and a protein-fixed biochip is called as a protein chip. Also a biochip is broadly classified into a microarray chip and a microfluidics chip. A microarray chip is a biochip where thousands or scores of thousands of DNAs, proteins, etc. are attached at regular intervals and process a target material to be analyzed on the chip, and analyze the bonding pattern. A DNA chip, a protein chip or the like are the representative microarray chip. A microfluidics chip is also called as a lab-on-a-chip, which can analyze a reacting pattern by injecting a very small amount of target material to be analyzed and observing various bio-molecular probes or sensors fixed on the chip. A DNA chip is classified into an oligonucleotide chip, a cDNA chip, a PNA chip, etc. according to the kind of probes to be fixed. A oligonucleotide chip is a new technique for probing genetic diversity on a large scale, in which a large number of synthetic oligonucleotides are attached to a certain correct position of a very small space of a support and hybridizes with a very small amount of target base sequence so that many genes can be searched at the same time. Such an oligonucleotide chip is expected to make a major contribution to a drug-resistant diagnosis, mutant search, single nucleotide polymorphism (SNP), a disease diagnosis or genotyping.

A biosensor can be classified as roughly six application fields as follows.

1. Clinical diagnosis and medical field: This field takes up about 90% of the overall biosensor market. It is mostly occupied by a glucose sensor for sensing blood sugar, but a market share of the biosensors capable of sensing various biomaterials such as lactic acid, cholesterol, urea, etc. is expected to become high since a demand for point-of-care testing (POCT) rapidly increases.

2. Environment: A biosensor is used for detecting an environment-related substance such as an endocrine disruptor, a biochemical oxygen demand (BOD) of waste water, a heavy metal, an agricultural chemical, etc. Researches on a sensor that has selectivity to various endocrine disruptors such as dioxin and is capable of sensing low concentration have been in progress from various angles.

3. Food: A biosensor is applied to food safety inspection, for example, for use in detection of hazardous substances such as residual agricultural chemicals, antibiotics, pathogens, a heavy metal, etc.

4. Military: A biosensor is used for sensing a biochemical weapon for mass destruction, such as sarin, anthrax, etc. To cope with a biological weapon, a biosensor requires quick sensing time and miniaturization to be used in a field.

5. Industry: A biosensor is used for controlling a growing condition of a microorganism in a fermentation process, or for monitoring specific chemical substances generated in chemistry/petro-chemistry, pharmaceuticals, and food processing, etc.

6. Researches: A biosensor is used for analyzing the speed of bonding between biomaterials, and sensing the behavior of a single molecule.

An electric field effect transistor is a device which is used to convert a voltage signal inputting to a gate electrode into an electric current signal to outputting from a source electrode or a drain electrode. An electric field effect refers to a phenomenon that when an electric field is applied to the semiconductor, a conductive channel is formed so that electricity can flow as carriers (free electrons or holes) within a semiconductor move depending on the applied electric field in such a manner that (−) carriers, i.e., electrons are collected in a (+) side, and (+) carriers, i.e., holes are collected in a (−) side.

Where voltage is applied between the source and drain electrodes, charged particles existing in a channel move along a direction of the electric field between the source electrode and the drain electrode, and then voltage is outputted as a current signal from the source electrode or the drain electrode. At this time, the intensity of the outputted electric signal is proportional to the density of the charged particles. Where voltage is applied to a gate electrode installed on the top, laterals, bottom, etc. of a channel through an insulator, the density of the charged particles existing in the channel is changed. Upon this fact, by changing gate voltage, an electric current signal is changed.

A carbon nanotube has electric conductivity as excellent as copper, thermal conductivity as excellent as diamond, strength a hundred times higher than a steel with a ⅙ weight, and strain resistant to breaking. A carbon nanotube, discovered by Japanese Dr. Iijima in 1991, shows several unique quantum mechanical phenomena due to a quasi-one-dimensional quantum structure; and has characteristics such as a very small diameter of several to several tens of nanometers (nm), a large length to diameter ratio, and a hollow structure. Due to a very unique one-dimensional carbon structure, the carbon nanotube has excellent mechanical, thermal, electrical properties, and is evaluated as a new material for the next-generation. Due to lots of merits thereof, particularly, the excellent mechanical properties and the high electric and thermal conductivities, a variety of applications of the carbon nanotube to an electric field effect transistor, a flat panel display device, an electronic device, etc. have been researched throughout industry. Further, an attempt to apply the carbon nanotube to a biosensor has increased.

For example, the application to a transistor device has been researched as follows. In 1998, researchers of Delft University of Technology in the Netherlands materialized the carbon nanotube as a transistor that operates at a room temperature (Sander J. Tans et al., *Nature*, 1998, 393, 49). The experimental result shows that an electronic device based on the carbon nanotube which has excellent properties in the physical and electrical aspects can operate a hundred times faster, can be more highly integrated, and can have lower power-loss than a conventional electronic device based on silicon. This is the first instance that shows applicability in an electronic device based on a carbon nanotube in the future.

Thereafter, various applications of a nano-devices based on the carbon nanotube has been presented by many research institutions all over the world through a lot of papers, patents, etc. up to now (as of 2009). In 2009, group researchers of Harvard University in the U.S.A. introduced an experimental result of a highly-sensitive measurement of change in a surface charge of a biomaterial, using a carbon nanotube as a channel in a biosensor based on an electric field effect transistor (Charles M. Liber et al., *Science*, 2001, 293, 1289). Since then, developed technology made it possible to measure a large change in the surface charge through enzyme reaction, and then to measure a minute change in the surface charge of protein-protein bonding. Recently, the technology has reached measuring a change in a surface field due to approach of protein. In 2005, researchers of Chungnam National University in Korea and Korea Research Institute of Chemical Technology introduced a concept of the biosensor using the carbon nanotube-electric field effect transistor (CNT-FET). This is based on the feature that electric conductivity through a carbon nanotube decreases while the negative charges of an aptamer disappears when a DNA aptamer is attached on the surface of a carbon nanotube using CDA-Tween 20, as a linker, which materializes a high-performance CNT-FET biosensor capable of measuring a certain target molecule at a level of 10 nM (Hye-Mi So, et al., *J AM. Chem. Soc.*, 2005, 34, 11906). By ongoing researches, it is announced that the sensitivity enhances as a bonding distance between the surface of the carbon nanotube and a biomaterial to be detected becomes close. By the research, the industrial applicability of the technology has increased by succeeding IgE detection of 1.8 nM using a CNT-FET sensor (Kenzo Maehashi, et al., Anal. Chem., 2007, 79, 782).

Korean Patent First Publication No. 2007-53545 relates to a technique in which the conductivity is increased by the carbon nanotube attached to a target molecule when the target molecule hybridizes with a probe, and thus it is possible to easily detect the hybridization of the target molecule, which discloses a biochip including a top electrode, a bottom electrode and an insulating layer interposed between the top and bottom electrodes.

Korean Patent Registration No. 10-455284 relates to a technique in which respective receptors are arbitrarily fixed to a certain position on a chip by applying electric charges having opposed polarity to net charges of various receptors to be bonded with a target bio-molecule to a carbon nanotube after growing the carbon nanotube having a nanometer diameter on a non-conductive substrate, and thus high-integration or array with a desired pattern is possible at a nano ($10^{-9}$) level rather than a conventional array technology of a micro ($10^{-6}$) level, which discloses a nano-array type bio-molecule detecting sensor that includes a substrate and a plurality of carbon nanotubes arrayed on the substrate, in which the receptor to be bonded with the target bio-molecule is selectively attached onto the carbon nanotube at a desired position by applying an electric field to the carbon nanotube.

In addition, Korean Patent First Publication No. 2007-22165 discloses a sensor for detecting a detection target material through a field effect transistor which comprises a substrate, source and drain electrodes and a channel for a path of electric current between the source and drain electrodes, in which the electric field effect transistor includes an interaction sensing gate for fixing a certain material selectively interacting with the detection target material, and a gate to which voltage is applied to detect this interaction by a characteristic change of the electric field effect transistor.

However, despite such efforts of many researches, a research result for application of the biosensor using the carbon nanotube has not been disclosed yet with respect to the detection material having a low concentration of 1 nM or less.

SUMMARY OF THE INVENTION

Accordingly, it is desirable to provide a biosensor proper for detecting biomaterial (biomolecules) as a detection target material having a concentration of 1 nM or less.

Further, it is desirable to provide a method of producing a biosensor having the above features.

Further, it is desirable to provide a method of detecting a target biomaterial through the biosensor having the above features.

To this end, the present invention provides a biosensor for detecting a target biomaterial using the principle that contact resistance is changed as a receptor fixed on a detection area of a conductive material is selectively coupled with a detection target material and thus the amount of an electric current flowing from a source electrode to a drain electrode is changed, when using a carbon nanotube-electric field effect transistor to detect a biomaterial.

More specifically, according to an aspect of the present invention, there is provided a biosensor including a substrate, an insulating layer, source and drain electrodes formed on the insulating layer, a middle-discontinuous channel provided between the source and drain electrodes, and a detection area on which a detection target material is to be fixed, covering the middle-discontinuous section.

In a device according to an exemplary embodiment of the present invention, the substrate used for the biosensor is selected from a group including various non-conductive polymers such as silicon, glass, fused silica, quartz, plastics, polydimethylsiloxane (PDMS), etc. and combination thereof, but not limited thereto.

According to an exemplary embodiment, the insulating layer may include an electrical insulating material, and the electrical insulating material may include silicon dioxide ($SiO_2$), silicon nitride ($Si_3N_4$), Teflon®, polydimethylsiloxane (PDMS), and polymethylmethacrylate (PMMA), for example. The insulating layer may be formed in a part of the bottom, top and laterals of the channel.

The source and drain electrodes may be made of, for example, gold, silver, titanium, platinum, etc., but not limited thereto.

It is preferable that the middle-discontinuous channel is a carbon nanotube which has a semiconductor property.

According to an exemplary embodiment, the detection area on which the detection target material (target protein) is to be fixed may include a metal layer and a semiconductor layer, in which the metal layer may be made of a material selected from the group consisting of gold (Au), titanium (Ti), platinum (Pt), chrome (Cr), copper (Cu), aluminum (Al), palladium (Pd), Nickel (Ni) and combination thereof, and the semiconductor layer may be made of a material selected from the group consisting of silicon (Si) doped with p or n, zinc oxide (ZnO), gallium/arsenic (GaAs), gallium/nitrogen (GaN), indium/phosphorus (InP), etc., but not limited thereto in both cases. In this exemplary embodiment, the detection area serves as the gate electrode.

The biosensor includes a receptor fixed on the detection area and detects the biomaterial (biomolecules). The receptor refers to a material capable of interacting with the detection target material through specific bonding. If the detection target material interacts with the receptor fixed on the detection area through a specific bonding, the work function of the electrode is varied, and thereby contact resistance between the carbon nanotube and the detection area is changed. The change of the contact resistance affects flow of an electric current, which allows the detection target material to be detected.

On an interaction sensing gate, a lot of specific materials can be fixed. The interaction sensing gate on which a specific material is fixed may be preferably used in the biosensor for detecting a material that interacts with a functional material. Also, in order to amplify or specify a detected signal, a target material which interacts with the fixed specific material or a material which interacts with a target material can be labeled with an enzyme, a material having an electrochemical reaction or a light emitting reaction, a polymer and particles having a charge, etc., which is widely used as a labeling measurement method in DNA analysis, immunoassay, etc.

The "interaction" between a specific material and a detection target material indicates an action due to a force between molecules caused by at least one of a covalent bond, a hydrophobic bond, a hydrogen bond, a Van-der-Waals bond, a bond based on electrostatic force. However, the term "interaction" in this specification has to be interpreted in a broad sense, and not to be limitedly interpreted under any circumstances. A covalent bond includes a coordinate bond and a dipole bond. Also, a bond based on an electrostatic force includes electrical repulsion in addition to an electrostatic bond. Further, the interaction involves a bonding reaction, a synthetic reaction, and a decomposition reaction.

Specifically, the interaction includes binding and dissociation between an antigen and an antibody, binding and dissociation between a protein receptor and a ligand, binding and dissociation between a bonding molecule and a counterpart molecule, binding and dissociation between an enzyme and a substrate, binding and dissociation between an apo-enzyme and a co-enzyme, binding and dissociation between nucleic acid and protein bonded thereto, binding and dissociation between nucleic acid and nucleic acid, binding and dissociation between protein and protein in an information transmission system, binding and dissociation between glycoprotein and protein, binding and dissociation between a cell/tissue and protein, binding and dissociation between a cell/tissue and a low-molecular compound, an interaction between an ion and an ion-sensitive material, etc., but not limited thereto. For example, the interaction may occur in immunoglobulin or its derivatives F(ab')2, Fab', Fab, receptors or enzymes and their derivatives, nucleic acid, natural or artificial peptide, artificial polymer, carbohydrate, lipid, inorganic substances or organic ligands, viruses, cells, chemicals, etc.

A receptor is a biological substance that serves as a probe bonded with a target biomaterial to be detected, which is selected from a group consisting of nucleic acid(DNA, RNA, PNA, LNA and hybrid thereof), protein (enzyme, substrate, antigen, antibody, ligand, aptamer, etc.), a virus and an infectious disease, etc. For example, the receptor may be protein related to a disease.

According to an exemplary embodiment, a bonding additive for enhancing a bonding force between the carbon nanotube and the receptor may be applied directly before and after the receptor is attached to the carbon nanotube. Such a bonding additive functions to keep the bond between a carbon nanotube and a receptor even after an electric field is released from the carbon nanotube.

For example, the bonding additive may include a chemical substance where functional group such as aldehyde, amine, imine or etc. are attached to an end of a carbon; a monolayer such as $SiO_2$, $Si_3N_4$, etc.; a membrane such as nitrocellulose, etc.; or a polymer such as polyacrylamide gel, PDMS, etc.

According to an exemplary embodiment, a hydrophobic material, such as, Teflon, polydimethylsiloxane (PDMS), polymethylmethacrylate (PMMA), silicon dioxide ($SiO_2$) and silicon nitride ($Si_3N_4$) is provided between the source electrode and the detection area and between the drain electrode and the detection area. Preferably, Teflon is provided to prevent a target biomaterial from contacting the source electrode and the drain electrode.

The electric field effect transistor formed as above can detect a biomaterial having a low concentration of 1 nM or less, which will be ascertained in the exemplary embodiments to be described below. This is estimated to be based on a Schottky barrier effect due to the enlargement of a Schottky contact area and a chemical gating effect of a chemical compound. That is, the contact resistance and the Schottky barrier having a length of about 1 mm in a contact section between the carbon nanotube (CNT) (forming the Schottky barrier) disposed between opposite ends of a gold (Au) layer, on which the detection-target material is to be placed, and an electrode layer, where the electrode is formed, is more enlarged than that of a conventional structure. It is regarded that a biomaterial can be detected with high sensitivity, due to the enlarged Schottky barrier and the chemical gating effect.

The Schottky barrier and the chemical barrier effect will be described in short. The Schottky barrier means a potential barrier of rectification on a junction between a metal and a semiconductor. The Schottky barrier is different from a p-n junction in that contact voltage is relatively low and a depletion region of the metal is decreased. The Schottky barrier is not always formed in contact between all kinds of metals and a semiconductor. However, in the present exemplary embodiment, the carbon nanotube acts like a p-type semiconductor, and the Schottky barrier is formed on the junction when the carbon nanotube contacts the metal. Further, it is estimated that the Schottky barrier is varied when detecting a biomaterial in a gold (Au) island and thus an electric signal is increased or decreased in addition to the chemical gating effect, as a result, a biomaterial is detected. The Schottky barrier is classified into an ohmic contact and a rectifying contact according to the kind of the semiconductor and a relative work function between the metal and the semiconductor.

$\Phi M>\Phi S$ (n-type semiconductor): rectifying contact
$\Phi M<\Phi S$ (n-type semiconductor): ohmic contact
$\Phi M>\Phi S$ (n-type semiconductor): ohmic contact
$\Phi M<\Phi S$ (p-type semiconductor): rectifying contact The chemical gating effect is a method of imitating the electric field effect of the electric field effect transistor through chemical substances, and uses gas, or molecules or substances having charges at a surface thereof. For example, when a device made of the carbon nanotube is exposed to $NH_3$, $NH_3$ provides electrons while being adsorbed onto the carbon nanotube and thus the number of holes as the existing carriers is decreased. At the same time, a valence band is lowered from a Fermi level, thereby conductivity decreases. Likewise, if bio-molecules approach the carbon nanotube while having a certain electric charge, the conductivity of the carbon nanotube is varied.

Another aspect of the present invention, there is provided a method of producing a carbon nanotube-field effect transistor (CNT-FET), the method including the steps of preparing a substrate; forming an insulating layer on the substrate; depositing a carbon nanotube with a discontinuous middle channel on the insulating layer; depositing a conductive material to form a source electrode and a drain electrode; depositing a metal and a semi-conductive material on a detection area to which a detection target material is to be fixed, covering a middle-discontinuous channel; and supplying electric power through conductive nanowires for respectively applying electric charges to the source and drain electrodes.

According to an exemplary embodiment, Teflon is provided between the detection area and the source electrode and between the detection area and the drain electrode after forming the detection area, so that a target biomaterial to be detected can be prevented from contacting the source electrode and the drain electrode by the hydrophobic properties of Teflon.

The carbon nanotube is deposited in the form of a network or a Langmuir-Blodgett film. The carbon nanotube is grown by chemical vapor deposition (CVD), laser ablation, or arc-discharge, formed by coating the substrate with carbon nanotube paste, or deposited by electrophoresis or a filtering method. The carbon nanotube may be a single-walled nanotube, a double-walled nanotube, a multi-walled nanotube, or a rope nanotube. The carbon nanotube may use a network structure formed through a filtering method or a film which is excellent in array and having directionality, formed by a Langmuir-Blodgett method.

The middle-discontinuous section of the carbon nanotube is formed to have a distance of 10-2000 μm. Preferably, the middle-discontinuous section is formed to have a distance of 1000-1500 μm. The present inventors have found out that the biosensor has shown the best sensibility in the above range of distance.

Each distance between the source electrode and the detection area and between the drain electrode and the detection area is of 0.5-2.0 mm so that the Schottky contact area can be largely formed. As the Schottky contact area is largely formed, it is estimated that the device in this exemplary embodiment has an effect of detecting the biomaterial with high sensitivity in addition to the chemical gating effect.

The metal may be deposited on the source and drain electrodes by physical vapor deposition (PVD), e-beam evaporation, or thermal evaporation. Preferably, the metal may be deposited by the thermal evaporation.

The metal used for the electrodes is the same as above. Preferably, gold (Au) or titanium (Ti) is used as a metal.

If the receptor capable of specifically bonding with and interacting with the detection target material is included in the detection area of the biosensor having the foregoing features, the work function of the electrode is varied depending on the interaction, and thus the contact resistance between the carbon nanotube and the detection area is varied. The variation of the contact resistance affects the flow of the electric current, which makes it possible to detect the detection target material.

The receptor may be fixed to the detection area by physical or chemical bonding. For instance, a thiol group of the receptor may be bonded to the detection area consisting of gold (Au).

The foregoing biosensor according to the exemplary embodiments is provided with a more enlarged Schottky contact area so that biomaterials of various contents having a low concentration of 1 nM or less can be detected with high sensitivity.

BRIEF DESCRIPTION OF THE DRAWINGS

The above and/or other aspects will become apparent and more easily appreciated from the following description of the exemplary embodiments, taken in conjunction with the accompanying drawings, in which.

DETAILED DESCRIPTION OF EXEMPLARY EMBODIMENTS

Below, exemplary embodiments will be described in detail with reference to accompanying drawings. The following exemplary embodiments are given by way of example and do not limit the scope of the invention.

A carbon nanotube-electric field effect transistor according to an exemplary embodiment is manufactured as follows.

A silicon wafer is prepared to be used as a substrate, and then a layer of silicon dioxide is deposited as an insulating layer on the substrate. On the insulating layer, a carbon nanotube is deposited to be discontinued by a distance 1500 µm in the middle thereof. The carbon nanotube is deposited in the form of a Langmuir-Blodgett film, and a single-walled nanotube is used. Also, the carbon nanotube is grown by chemical vapor deposition (CVD). To form source and drain electrodes, gold (Au) is deposited. Gold is deposited to form a detection area to which a detection target material is to be fixed, covering the middle-discontinuous section of the carbon nanotube. The gold forming the detection area is distant from each of the source and drain electrodes by 1 mm. Then, electric power is supplied through nanowires to respectively apply electric charges to the source and drain electrodes.

Figure 1:
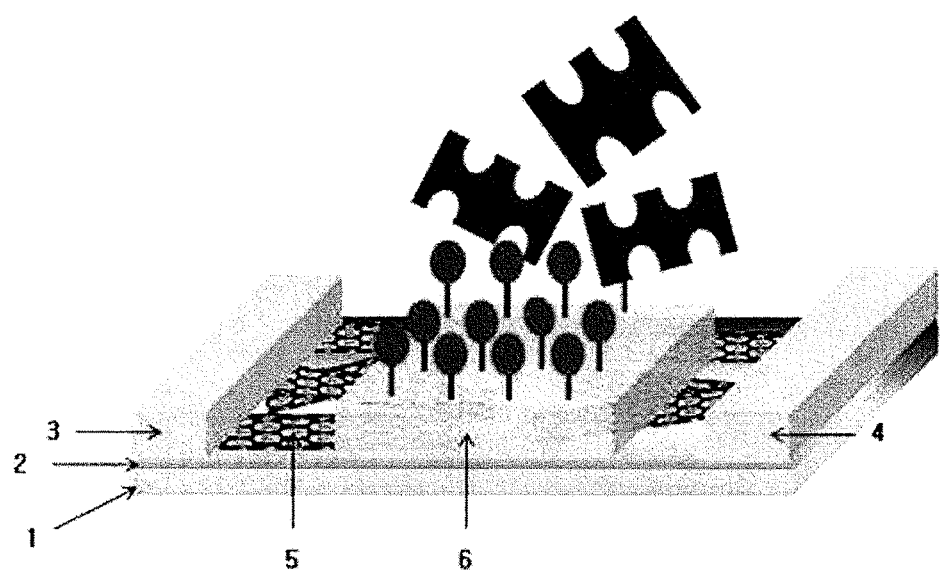
FIG. 1 is a schematic view of a biosensor based on a carbon nanotube-electric field effect transistor according to an exemplary embodiment, showing a use pattern.

FIG. 1 is a schematic view of a biosensor manufactured according to an exemplary embodiment. In FIG. 1, a receptor to be fixed on a detection area and a biomaterial to be specifically bonded with the receptor are shown.

Figure 2:
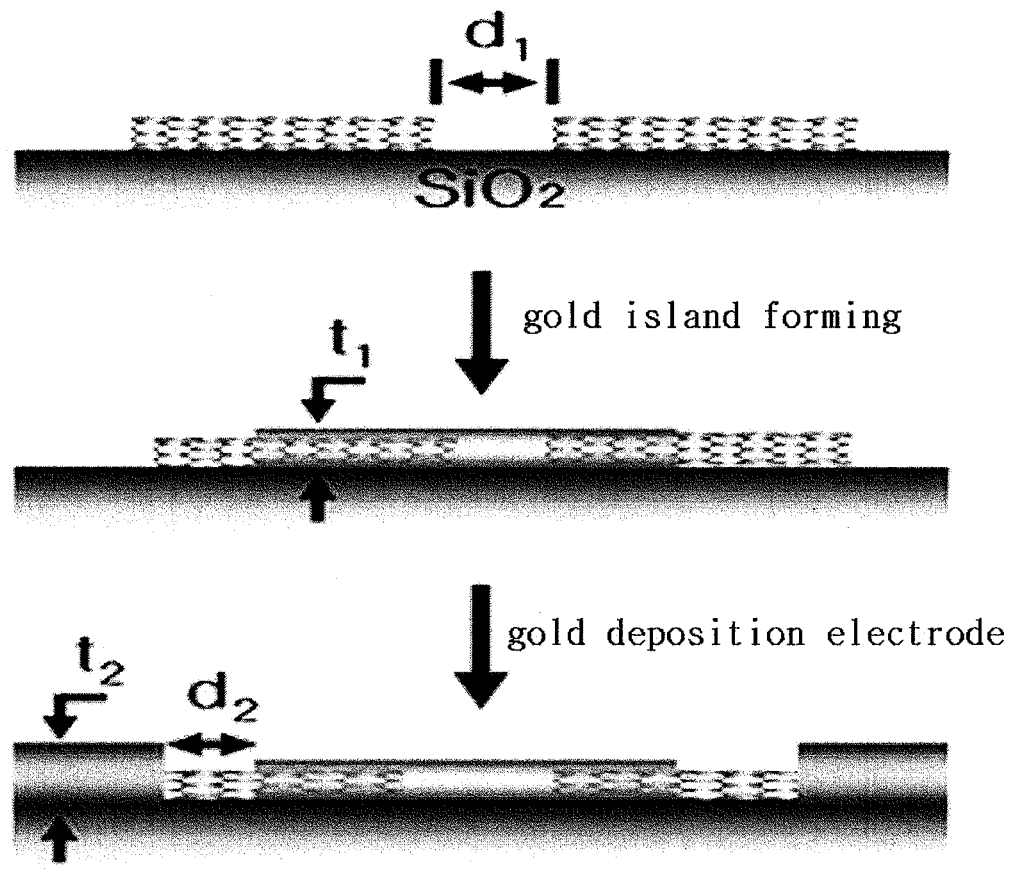
FIG. 2 is a schematic view showing a method of producing a biosensor based on a carbon nanotube-electric field effect transistor according to an exemplary embodiment.

Referring to FIG. 2 which is a schematic view of manufacturing the biosensor according to an exemplary embodiment, a single-walled carbon nanotube is used as a channel on an $SiO_2$/Si substrate, and gold (Au) is deposited between an electrode and a discontinuous carbon nanotube to which a detection target material is fixed.

Figure 3:
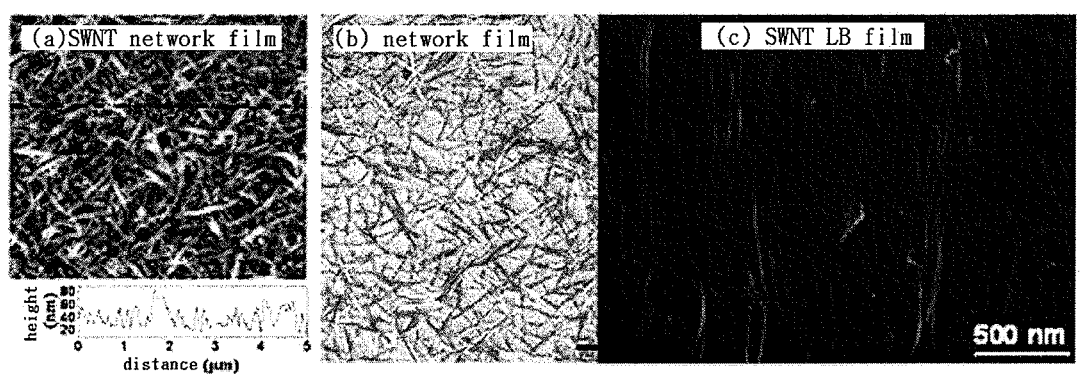
FIG. 3 (*a*) shows an atomic force microscopy (AFM) image where a carbon nanotube connecting a gold (Au) layer to which a detection target material to be attached with an electrode has a network structure in the device manufactured in FIG. 2, and shows the height of the section thereof, FIG. 3 (*b*) shows a scanning electron microscopy (SEM) image of the network carbon nanotube, and FIG. 3 (*c*) is an SEM image showing that the carbon nanotube of the manufactured device can be arrayed by a Langmuir-Blodgett method and formed as a film having directionality.

In the upper part of FIG. 3 (a) shows an atomic force microscopy (AFM) image where the carbon nanotube connecting the gold (Au) layer to which the detection material is to be attached with the electrode has a network structure in the device manufactured in FIG. 2. Further, the height of the section thereof is shown in a lower area of FIG. 3 (a). FIG. 3 (b) shows a scanning electron microscopy (SEM) image of the network carbon nanotube. Referring to FIG. 3 (c), the SEM image shows that the carbon nanotube of the manufactured device can be arrayed by a Langmuir-Blodgett method and formed as a film having directionality.

Figure 4:
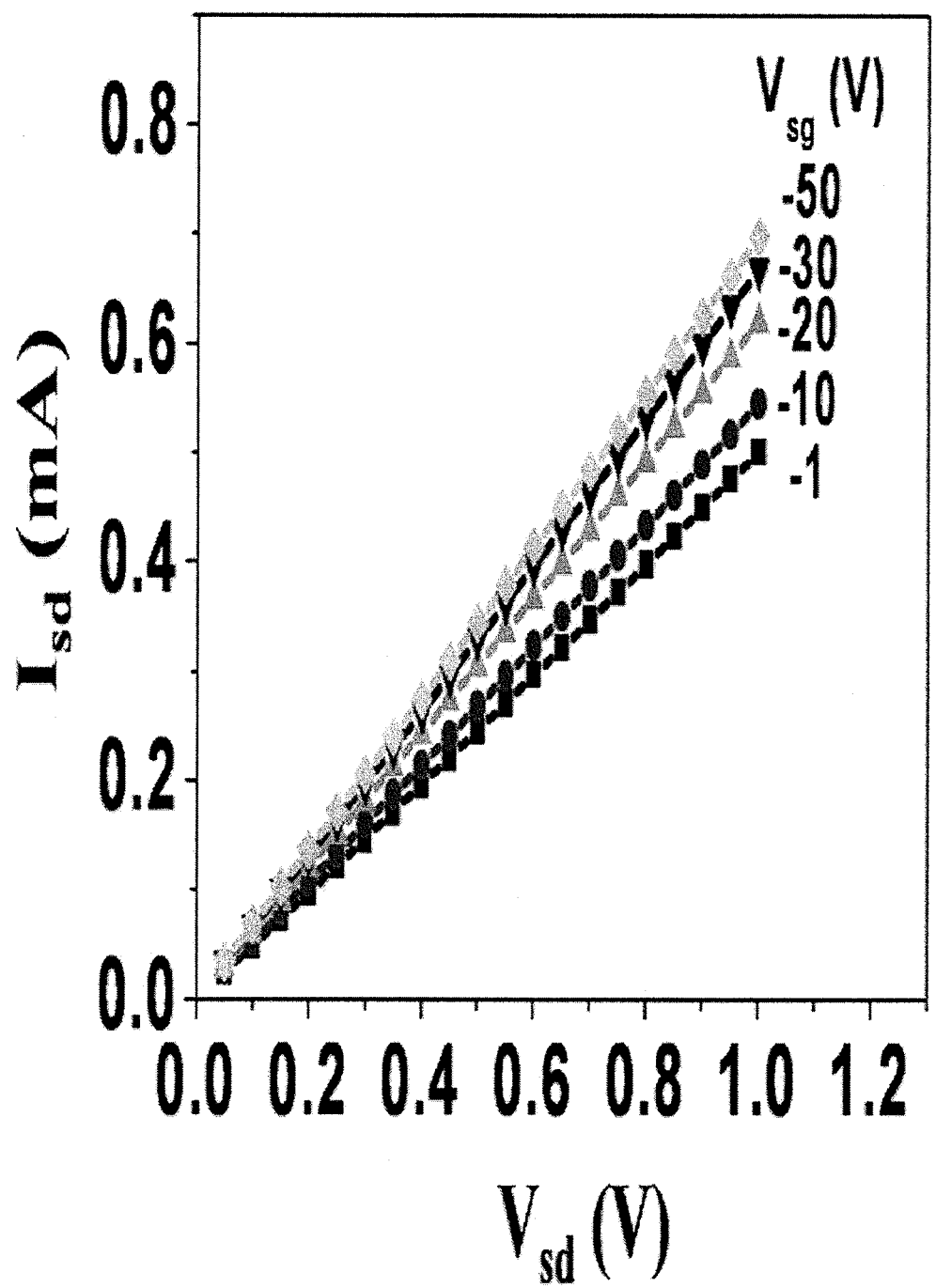
FIG. 4 is a graph showing that an electric current flowing in a network-structured carbon nanotube channel of the device manufactured according to an exemplary embodiment is varied depending on applied gate voltage.

Referring to a graph of FIG. 4, an electric current flowing in the channel of the device made of the network carbon nanotube manufactured as shown in FIG. 2. FIG. 4 shows that electric current is varied depending on a gate voltage applied thereto. It also shows I-V characteristics of metal-semiconductor in the carbon nanotube-electric field effect transistor (CNT-FET).

A method of detecting a target biomaterial through the biosensor manufactured as described above according to an exemplary embodiment is as follows.

Figure 5:
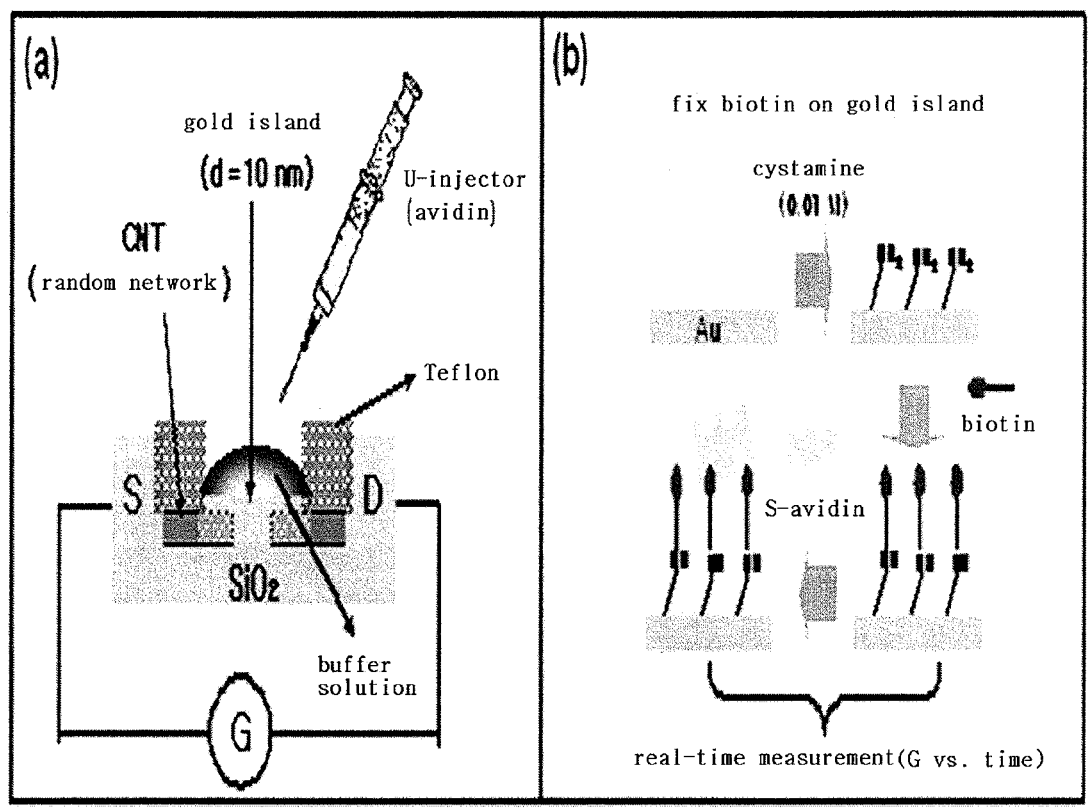
FIG. 5 (a) schematically shows a method of detecting protein through a Teflon cell according to an exemplary embodiment, and FIG. 5 (b) schematically shows that streptavidin protein as target protein is specifically bonded with biotin fixed as a probe on a device protected by bovine serum albumin (BSA) protein.

Referring to FIG. 5 (a), a preparation for measurement of an electric current variation through the biosensor according to an exemplary embodiment is firstly performed, in which the detection area is blocked by a Teflon cell from each of the source and drain electrodes. Then, as shown in FIG. 5 (b), streptavidin protein as target protein is specifically bonded with biotin fixed as a probe on the device protected by bovineserumalbumin (BSA) protein.

In FIGS. 5 (a) and (b), Teflon cells are installed to the carbon nanotube-electric field effect transistor, and then variation in an electric current of the device is measured while applying a bias voltage (Vds) of 0.1V between the source and drain electrodes and filling the device with phosphate buffer solution (PBS, 10 mM, pH=7.4) and different protein solutions.

Figure 6:
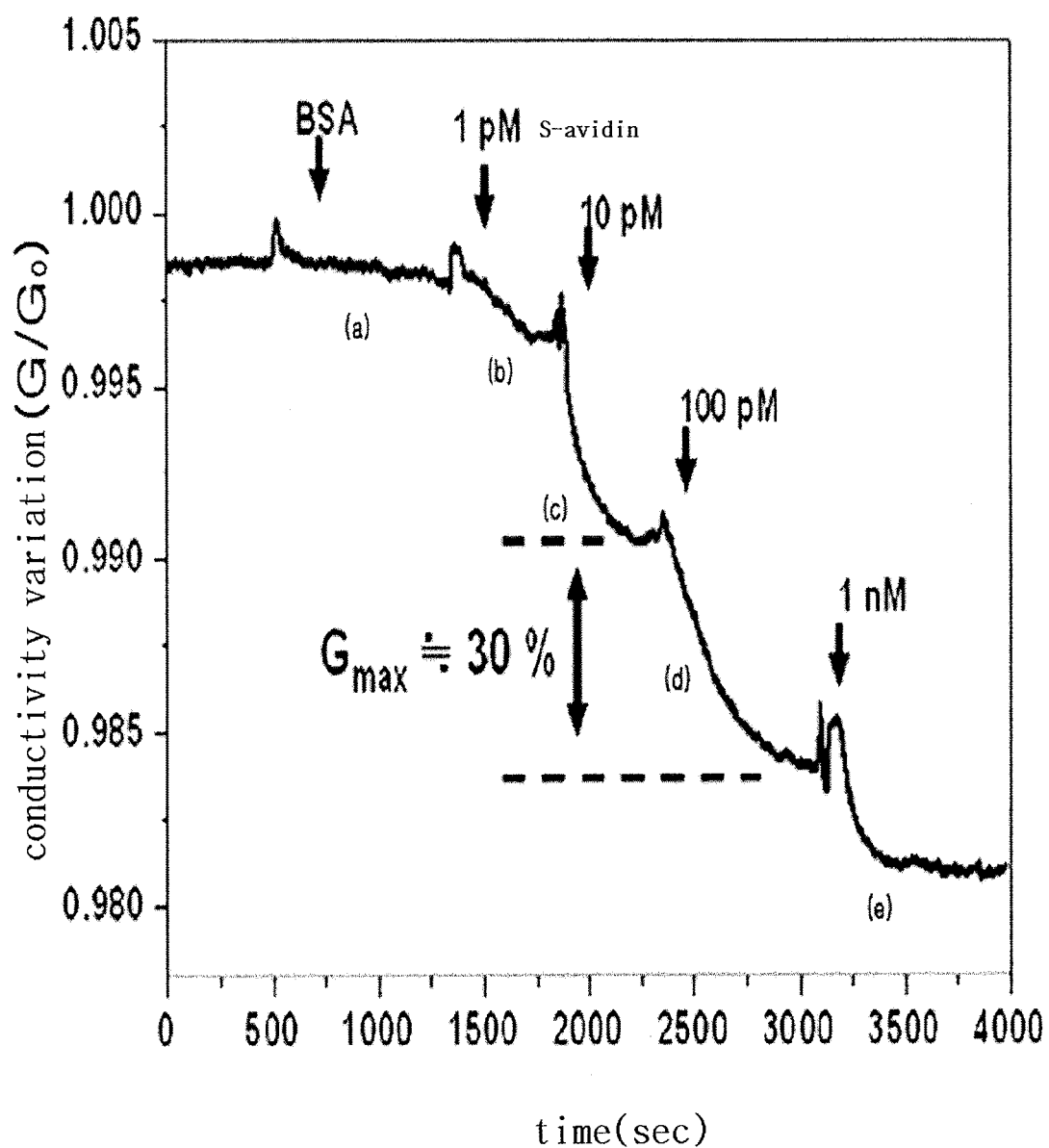
FIG. 6 is a graph showing a conductance drop of a device with regard to a specific recognition reaction between biotin and streptavidin, in which a section (6) a shows that there is no change in an electric signal when the bovine serum albumin (BSA) protein, which does not specifically react with a biotin molecule, is applied to the device, and sections (b) to (e) show a conductance drop even in the minimum concentration of 1 pM at the time of specific reactions of the streptavidin protein in different concentrations.

A graph of FIG. 6 shows a conductance drop in real time by the interaction mechanism of avidin's specific recognition of biotin-through the structure of FIG. 5 (a). In case of a section (a) in FIG. 6, there is no change in an electric signal when the bovineserumalbumin (BSA) protein, which does not specifically react with a biotin molecule, is applied to the device. Sections (b) to (e) in FIG. 6 respectively show conductance drops even in the minimum concentration of 1 pM when the streptavidin protein specifically reacts with biotin in various concentrations.

As described above, in producing a detecting sensor of biomaterial, the structure in which a gold layer exists between source electrode and drain electrode, and a middle-discontinuous carbon nanotube which connects the above two electrodes is provided makes it possible to detect a biomaterial having a concentration of 1 nM or less through enlarged Schottky contact area, plentiful semiconductor-properties carbon nanotube, Schottky contact area between metal-semiconductor nanotubes, their contact resistance, and the contact resistance between nanotube.

Although some exemplary embodiments have been shown and described, it will be appreciated by those skilled in the art that changes may be made in these exemplary embodiments without departing from the principles and spirit of the invention, the scope of which should be defined in the appended claims and their equivalents.

What is claimed is:

1. A biosensor based on a carbon nanotube-electric field effect transistor, the biosensor comprising a substrate, an insulating layer, source and drain electrodes formed on the insulating layer, a middle-discontinuous channel provided between the source and drain electrodes, and a detection area on which a detection target material is to be fixed, covering a middle-discontinuous section of the channel to form a Schottky barrier, wherein the detection area is distant from each of the source electrode and the drain electrode by 0.5-2.0 mm, wherein:
   the middle-discontinuous channel comprises a first semiconductor structure spaced apart from a second semiconductor structure;
   the middle-discontinuous channel has a discontinuous distance ($d_i$) of 10-2000 µm in the middle thereof;
   the detection area comprises a metal;
   the first semiconductor structure and the second semiconductor structure are coupled by the conductive material; and the Schottky barrier is formed between the metal and the first and second semiconductors.

2. The biosensor according to claim 1, wherein Teflon®, polydimethylsiloxane (PDMS), polymethylmethacrylate (PMMA), silicon dioxide (SiO2), or silicon nitride (Si3N4), which is a layer of hydrophobic material separate from the insulating layer, is provided between the source electrode and the detection area and between the drain electrode and the detection area.

3. The biosensor according to claim 2, wherein the hydrophobic material is Teflon.

4. The biosensor according to claim 1 or 2, wherein the carbon nanotube comprises a network formed using chemical vapor deposition (CVD), laser ablation, arc-discharge, carbon nanotube (CNT) paste, electrophoresis, or a filtering method, or comprises a film formed using a Langmuir-Blodgett method.

5. The biosensor according to claim 1 or 2, wherein the detection target material is selected from a group consisting of nucleic acids (DNA, RNA, PNA, LNA and their hybrid), protein (enzyme, substrate, antigen, antibody, ligand, aptamer, etc.), a virus and an infectious disease.

6. The biosensor according to claim 1 or 2, wherein the detection target material comprises protein related to a disease.

7. The biosensor according to claim 1 or 2, wherein a bonding additive for enhancing the bonding force between the carbon nanotube or the detection area and a receptor is given before and after attaching the receptor to the carbon nanotube or the detection area.

8. A method of producing a biosensor according to claim 1, based on a carbon nanotube field effect transistor, comprising the steps of: preparing a substrate; forming an insulating layer on the substrate; depositing a carbon nanotube with a discontinuous middle channel on the insulating layer; depositing a conductive material to form a source electrode and a drain electrode; depositing a metal and a semi-conductive material on a detection area on which a detection target material is to be fixed, covering the middle-discontinuous channel; and supplying electric power through conductive nanowires to respectively apply electric charges to the source and the drain electrodes.

9. The method according to claim 8, wherein Teflon®, polydimethylsiloxane (PDMS), polymethylmethacrylate (PMMA), silicon dioxide (SiO2), or silicon nitride (Si3N4), which is a hydrophobic material, is provided between the source electrode and the detection area and between the drain electrode and the detection area, to prevent a target biomaterial from contacting the source electrode and the drain electrode.

10. The method according to claim 8 or 9, wherein the hydrophobic material is Teflon.

11. The method according to claim 8 or 9, wherein the metal is deposited on the source and drain electrodes by physical vapor deposition (PVD), e-beam evaporation, or thermal evaporation.

12. A method of detecting a biomaterial using the biosensor according to any one of claim 1 or 2.

* * * * *